United States Patent [19]

Hench et al.

[11] Patent Number: 5,074,916
[45] Date of Patent: Dec. 24, 1991

[54] ALKALI-FREE BIOACTIVE SOL-GEL COMPOSITIONS

[75] Inventors: Larry L. Hench; Arthur E. Clark; Rounan Li, all of Gainesville, Fla.

[73] Assignee: Geltech, Inc., Alachua, Fla.

[21] Appl. No.: 525,539

[22] Filed: May 18, 1990

[51] Int. Cl.$^5$ .................. C09K 3/00; C01B 15/16; C03C 10/00; C04B 38/00

[52] U.S. Cl. .................. 106/35; 423/308; 423/311; 501/2; 501/5; 501/10; 501/63; 501/72; 501/80; 623/11; 623/16

[58] Field of Search .................. 501/10, 63, 72, 80, 501/5, 2; 623/16, 11; 106/35; 423/308, 311

[56] References Cited

U.S. PATENT DOCUMENTS

| | | |
|---|---|---|
| 3,922,155 | 11/1975 | Broemer et al. . |
| 3,981,736 | 9/1976 | Broemer et al. ............ 501/10 |
| 4,120,730 | 10/1978 | Trojer et al. ............ 501/5 |
| 4,171,544 | 10/1979 | Hench et al. . |
| 4,189,325 | 2/1980 | Barrett et al. . |
| 4,234,972 | 11/1980 | Hench et al. . |
| 4,366,253 | 12/1982 | Yagi ............ 501/10 |
| 4,478,904 | 10/1984 | Ducheyne et al. . |
| 4,560,666 | 12/1985 | Yoshida et al. ............ 501/5 |
| 4,604,097 | 8/1986 | Graves, Jr. et al. . |
| 4,652,534 | 5/1987 | Kasuga ............ 501/10 |
| 4,698,318 | 10/1987 | Vogel et al. . |
| 4,737,411 | 4/1988 | Graves, Jr. et al. . |
| 4,775,646 | 10/1988 | Hench et al. . |
| 4,775,646 | 10/1988 | Hench et al. . |
| 4,783,429 | 11/1988 | Shibuya et al. . |
| 4,786,555 | 11/1988 | Howard, Jr. . |
| 4,851,046 | 7/1989 | Low et al. . |
| 4,871,384 | 10/1989 | Kasuga . |

OTHER PUBLICATIONS

Hench & Wilson, *Surface–Active Biomaterials*, 226 Science 630 (Nov. 9, 1984).

Hench & Paschall, *Direct Chemical Bond of Bioactive Glass–Ceramic Materials to Bone and Muscle*, 4 J. Biomed. Mater. Res. Symp. 25 (1973).

Hench, Splinter & Allen, *Bonding Mechanisms at the Interface of Ceramic Prosthetic Materials*, 2 J. Biomed. Mater. Res. Symp. 117 (1971).

Ogino, Ohuchi & Hench, *Compositional Dependence of the Formation of Calcium Phosphate Films on Bioglass*, 14 J. Biomed. Mat. Res. 55 (1980).

Hench & West, *The Sol–Gel Process*, 90 Chem. Rev. 33 (1990).

Hench, *Bioactive Ceramics*, in Bioceramics: Material Characteristics Versus in Vivo Behavior (1988).

*Primary Examiner*—Paul Lieberman
*Assistant Examiner*—William S. Parks
*Attorney, Agent, or Firm*—Cesari and McKenna

[57] ABSTRACT

Sol-gel processing techniques are used to produce alkali-free bioactive glass compositions based on $SiO_2$, CaO and $P_2O_5$. By varying the $SiO_2$ content, a range of hydroxyapatite production rates can be obtained; conversely, varying the time of exposure to actual or simulated in vivo solutions permits use of a range of allowable proportions of $SiO_2$. The sol-gel derived compositions can be chosen to achieve target values for thermal expansion coefficient, elastic modulus and volume electrical resistivity.

6 Claims, 10 Drawing Sheets

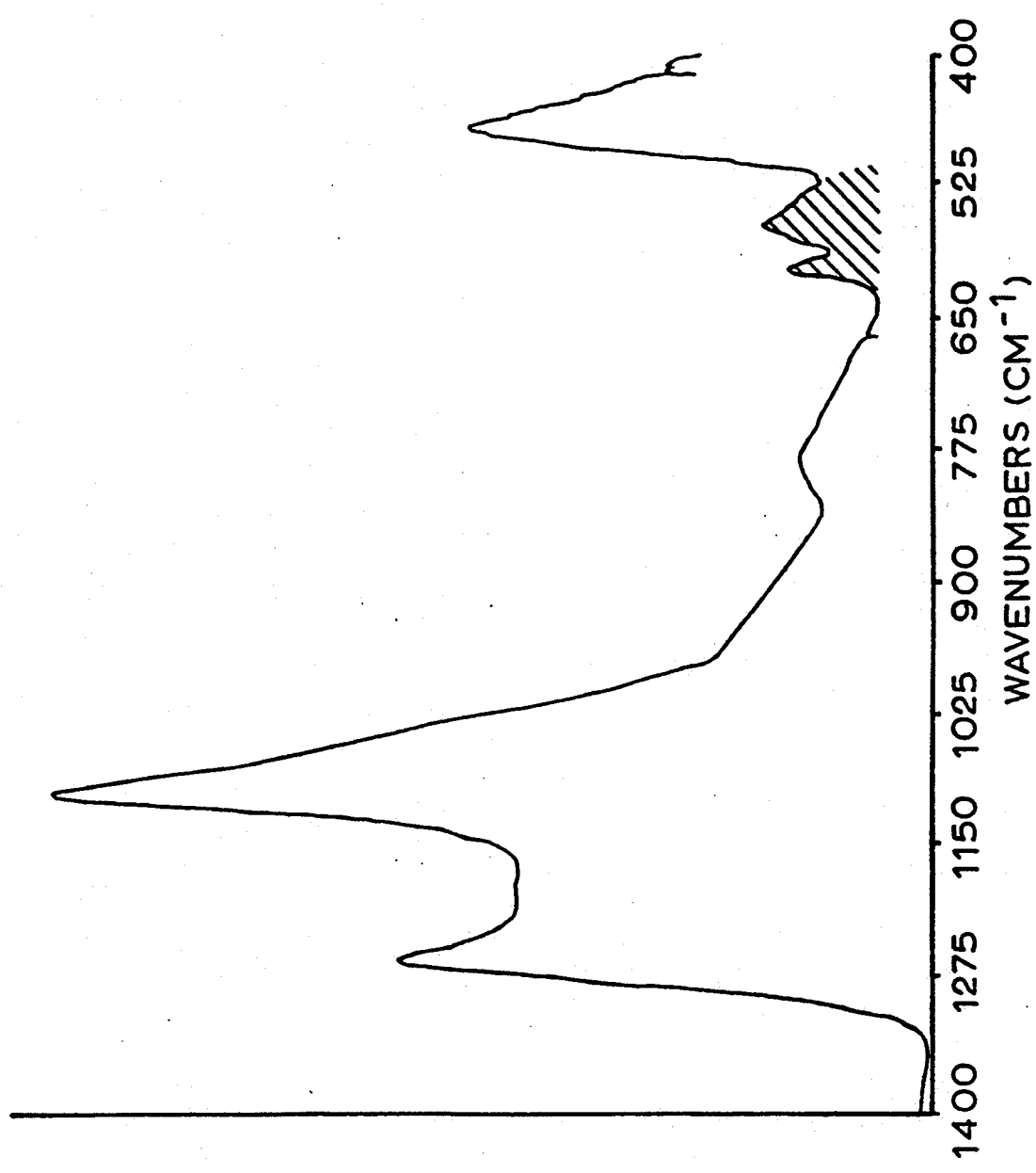

ALKALI-FREE BIOACTIVE SOL-GEL COMPOSITIONS

BACKGROUND OF THE INVENTION

A. Field of the Invention

The present invention relates to biocompatible glass compositions, and more particularly to alkali-free compositions produced by a sol-gel process.

B. Description of the Prior Art

Bioactivity is a unique property associated with the ability of a synthetic material to bond with living tissue. All materials implanted in vivo elicit a response from the surrounding tissue. Four types of response are possible: (i) if the material is toxic, the tissue dies; (ii) if the material is nontoxic and dissolves, the surrounding tissue replaces it; (iii) if the material is nontoxic and biologically inactive, a fibrous tissue capsule of variable thickness forms; and (iv) if the material is nontoxic and biologically active, an interfacial bond forms. Bioactive materials are those which produce the fourth type of response.

Three key compositional features distinguish bioactive glasses from traditional soda-lime-silica glasses and provide the driving force for bonding with living tissues. Conventional bioactive glasses, which are well-characterized in the art, typically contain less than 60 mole percent $SiO_2$, high $Na_2O$ and $CaO$ content (20-25% each), and a high molar ratio of calcium to phosphorus (ranging around five). When such glasses are exposed to water or body fluids, several key reactions occur. The first is cation exchange, wherein interstitial $Na^{+1}$ and $Ca^{+2}$ ions from the glass are replaced by protons from solution, forming surface silanol groups and nonstoichiometric hydrogen-bonded complexes:

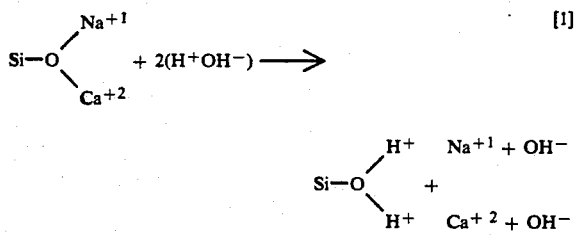

[1]

This cation exchange also increases the hydroxyl concentration of the solution, leading to attack of the fully dense silica glass network to produce additional silanol groups and controlled interfacial dissolution:

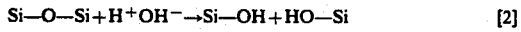

$$Si-O-Si + H^+OH^- \rightarrow Si-OH + HO-Si \qquad [2]$$

As the interfacial pH becomes more alkaline and the concentration of hydrolyzed surface silanol groups increases, the conformational dynamics attending high numbers of proximal silanol groups, combined with the absence of interstitial ions, cause these groups to repolymerize into a silica-rich surface layer:

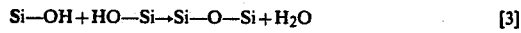

$$Si-OH + HO-Si \rightarrow Si-O-Si + H_2O \qquad [3]$$

Another consequence of alkaline pH at the glass-solution interface is crystallization into a mixed hydroxylapatite phase of the $CaO$ and $P_2O_5$ that were released into solution during the network dissolution of Equation 2. This takes place on the $SiO_2$ surface. The hydroxyapatite crystallites nucleate and bond to interfacial metabolites such as mucopolysaccharides, collagen and glycoproteins. It appears that incorporation of organic biological constituents within the growing hydroxyapatite- and $SiO_2$-rich layers triggers bonding to living tissues characteristic of bioactivity.

Currently, bioactive powders are produced by conventional processing techniques well-known in the art. The various constituents (e.g., reagent-grade $Na_2CO_3$, $CaCO_3$, $P_2O_5$ and $SiO_2$) are usually mixed in a suitable mixing device such as a rolling mill, and then heated in a platinum crucible to a temperature (generally between 1250 and 1400 degrees Centigrade) sufficient to cause the particles to melt and coalesce. See, e.g., U.S. Pat. No. 4,775,646; Ogino, Ohuchi & Hench, *Compositional Dependence of the Formation of Calcium Phosphate Films on Bioglass*, 14 J. Biomed. Mat. Res. 55, 56 (1980). The use of such high temperatures and specialized equipment results in significant production costs.

Conventional bioactive glasses suffer from other shortcomings in addition to high cost. These compositions tend to require an alkali metal oxide such as $Na_2O$ to serve as a flux or aid in melting or homogenization. However, the presence of alkali metal oxide ions results in a high pH at the interface between the glass and surrounding fluid or tissue; in vivo, this can induce inflammation. Furthermore, the rate of tissue repair, which drives the interfacial tissue-glass bonding promoted by bioactive material, tends to vary within a narrow pH range. If the surrounding environment grows too acidic or alkaline, repair shuts down, and interfacial bonding is defeated. Consequently, high rates of bioactivity (as measured by surface hydroxyapatite accretion) tend to be associated with significant local pH changes due to the release of alkali metal oxide ions, and have heretofore been avoided.

Conventional glasses also tend to be difficult to mix to homogeneity, a criterion that holds great importance for quality control of materials intended for implantation in the body. This is due to the relatively large grain size of the glass precursors, which generally measure approximately 10 to 1000 microns in diameter. It is difficult to obtain "molecular scale" mixing, i.e., homogeneity at the molecular level, using ordinary mixing techniques, such as stirring of the relatively viscous silicate melts.

Finally, for reasons discussed in more detail below, current bioactive powders cannot be prepared with a $SiO_2$ content greater than 60 mole percent. This limitation imposes a significant constraint on the producer's ability to tailor the material for a particular situation. It can be highly useful, for example, to vary the rate of hydroxyapatite formation, which is dependent upon $SiO_2$ content. As discussed above, the rate of metabolic tissue repair determines how quickly bonding between the tissue and a bioactive material can progress. Therefore, compatibility between the bioactive material and the surrounding tissue will be maximized when the material's bioactivity rate—that is, the speed with which hydroxyapatite is produced—matches the body's metabolic repair rate. However, an individual's repair rate can vary with age and disease state, among other factors, rendering identification of a single, ideal bioactivity rate impossible.

The $SiO_2$ level also determines the thermal expansion coefficient and elastic modulus of the glass. Particularly in the case of porous compositions, the ability to coat the glass onto a strong substrate (e.g., metal) significantly increases the range of clinical applications to which the glass will be amenable. Such coating is most conveniently accomplished when the thermal expansion coefficient of the glass matches that of the substrate, and restrictions on $SiO_2$ variation diminish the range of coefficients that may be achieved. Similarly, particular values or ranges for the elastic modulus can also be important in certain clinical applications (such as avoiding stress shielding of the repair of long bones and joints), rendering some glass compositions unsuitable if the $SiO_2$ level cannot be adjusted sufficiently.

DESCRIPTION OF THE INVENTION

A. Brief Summary of the Invention

The present invention utilizes sol-gel technology to synthesize bioactive glass powders from the system $SiO_2$—$CaO$—$P_2O_5$. The production of ceramic and glass materials by the sol-gel process has been known for many years. A "sol" is a dispersion of colloidal particles in a liquid, and the term "gel" connotes an interconnected, rigid network with pores of submicrometer dimensions and polymeric chains whose average length is greater than a micrometer. Basically, the sol-gel process involves mixing of the glass precursors into a sol; casting the mixture in a mold; gelation of the mixture, whereby the colloidal particles link together to become a porous three-dimensional network; aging of the gel to increase its strength; drying the liquid from the interconnected pore network; dehydration or chemical stabilization of the pore network; and densification, to produce structures with ranges of physical properties. See, e.g., Hench & West, *The Sol-Gel Process*, 90 Chem. Rev. 33 (1990).

All of these steps can generally be carried out at relatively low temperatures, as compared with traditional glassmaking techniques. Using the procedures described hereinbelow, our powders can be prepared from gels by sintering at 600-800 degrees Centrigrade without the use of platinum crucibles. Accordingly, these procedures afford cost-effective production.

The sol-gel process also permits use of very small colloidal particles (on the order of one nanometer or less) as glass precursors, thereby ensuring a high degree of homogeneity and purity in the final product.

Our formulations all involve only $SiO_2$, $CaO$ and $P_2O_5$; we have been able to eliminate the traditional need for sodium or other alkali metal compounds to assist in producing bioactivity. Not only does this reduce the glass from a four-component to a three-component system, but permits higher levels of bioactivity to be achieved without adverse interfacial pH consequences.

Another advantage of alkali-free formulations is increased volume electrical resistivity. While conventional bioglass compositions exhibit volume electrical resistivities of approximately $10^4$ ohm-centimeters, those associated with the present compositions are approximately $10^{10}$ ohm-centimeters. This attribute enhances the application of the invention for use as tissue-bonded electrical leads projecting into the neural system, such as cochlear implants for correction of profound deafness. The volume electrical resistivity of our compositions can be modified by altering the proportions of the constituents.

The amount of $SiO_2$ present in our formulations can be varied well beyond that associated with ordinary biocompatible glass compositions. This flexibility derives from the ultrastructural characteristics of the compositions of the present invention, which give rise to a large area density of nucleation sites for hydroxyapatite, and thereby permit use of smaller proportional amounts of $CaO$ and $P_2O_5$. We have discovered a relationship between reaction time and hydroxyapatite formation in our compositions that enables achievement of bioactivity for a target $SiO_2$ content by varying the duration of preliminary exposure to in-vivo conditions.

B. Brief Description of the Drawings

The foregoing discussion will be understood more readily from the following detailed description of the invention, when taken in conjunction with the accompanying drawings, in which:

FIG. 10 is an FTIR spectrum of the sol-gel derived bioactive powder represented as 86S in Table 1.

C. Detailed Description of the Invention

1) General Experimental Procedures

The glasses of the present invention are prepared from an alkoxysilane, preferably tetraethoxysilane ("TEOS"), an alkoxyphosphate, preferably triethylphosphate ("TEP"), and calcium nitrate using sol-gel preparation techniques. TEOS is first combined with water and nitric acid in a glass container, and covered. The amount of water added is critical, and depends on the degree of homogeneity desired, the amount of gelling, aging and drying time considered tolerable, and the importance of being able to form monoliths (which becomes progressively more difficult as the percentage of silica decreases).

We have found that by maintaining the molar ratio of water to TEOS plus TEP (i.e., $H_2O/(TEOS+TEP)$, hereinafter the "R ratio") between three and 10 (preferably eight), we were able to obtain complete hydrolysis (and therefore a homogeneous sol), reasonable gelation times (1-2 days), reasonable aging and drying times (2-4 days), and were able to prepare monoliths of the higher silica compositions. The range of R ratio facilitates preparation of coatings (at low R ratios), monoliths (at intermediate R ratios) and powders (at high R ratios).

The nitric acid (preferably 2N) is added to accelerate the hydrolysis reaction of TEOS. We employ a nitric acid volume approximately 1/6 that of the volume of water.

The remainder of the processing schedule must be controlled with some precision due to the unequal hydrolysis rates of the metal alkoxides. The components in the glass container (TEOS, nitric acid and water) are mixed, preferably using a magnetic stirring bar at medium speed. Although TEOS and water are initially immiscible, the solution becomes clear after 10-20 minutes.

After 60 minutes, TEP is added to the stirring solution. The calcium nitrate is added after another 60 minutes of mixing. The solution is then stirred for an additional hour, following which it is retained in a quiescent state for 20 minutes. During this period the material coalesces into a sol, which is thereafter introduced into polystyrene containers for casting. The containers are sealed with tape and placed into an oven for gelation and aging at 60 degrees Centigrade for 54 hours.

Figure 1:
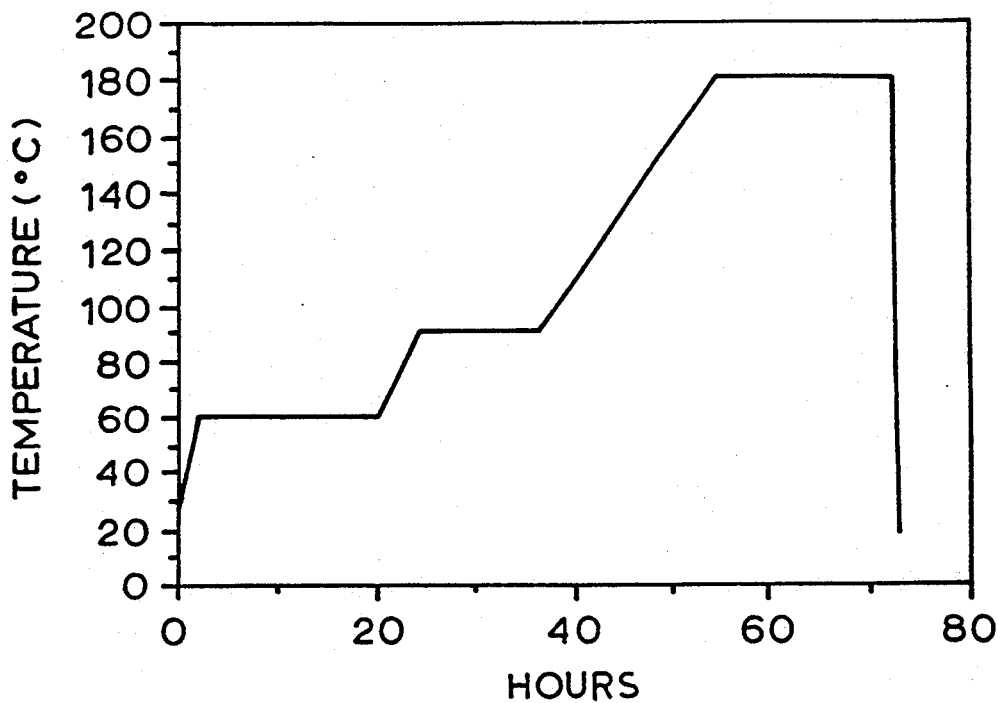
FIG. 1 is a drying schedule for all compositions listed in Table 1.

The samples are then removed from the aging chamber, placed in a glass container with a loose cover and the container introduced into a drying oven. We employ the drying schedule depicted graphically in FIG. 1 to make dried-gel powders. Although adherence to this schedule is not critical for powdered forms, a drying schedule must be rigidly adhered to in order to produce monoliths. Appropriate adjustment of the drying schedule to accommodate monolith production is well within the purview of one skilled in the art.

Figure 2:
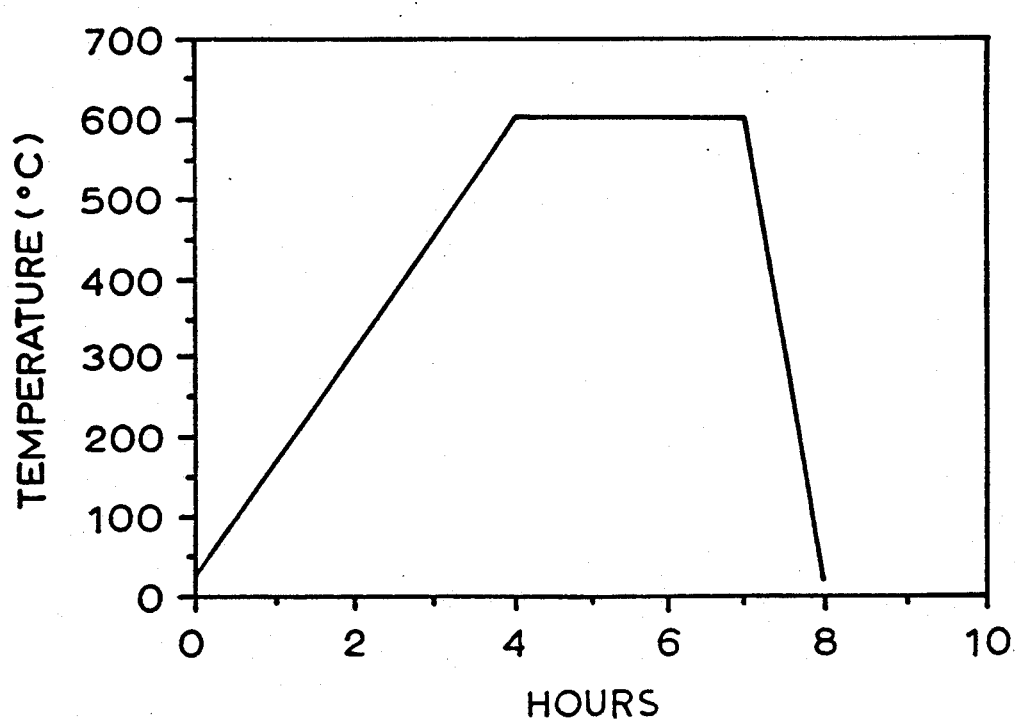
FIG. 2 is a calcination schedule for all compositions listed in Table 1.

The dried gel is placed in a quartz crucible for further calcination heat treatment. The calcination is carried out in a furnace through which is passed a slow flow of nitrogen gas. The purpose of the nitrogen is to avoid the formation and crystallization of carbonate hydroxylapatite during the heat treatment. Our calcination schedule is depicted graphically in FIG. 2.

2) Specific Examples and Analysis

Using the foregoing method, we have synthesized the compositions appearing in the following table:

TABLE 1

| Compositions of bioactive gel powders in mole % (in weight %) | | | |
| --- | --- | --- | --- |
| Sample | $SiO_2$ | $P_2O_5$ | CaO |
| 49S | 50(49) | 4(9) | 46(42) |
| 54S | 55(54) | 4(9) | 41(37) |
| 58S | 60(58) | 4(9) | 36(33) |
| 63S | 65(63) | 4(9) | 31(28) |
| 68S | 70(68) | 4(9) | 26(23) |
| 72S | 75(72) | 4(9) | 21(19) |
| 77S | 80(77) | 4(9) | 16(14) |
| 81S | 85(81) | 4(9) | 11(10) |
| 86S | 90(86) | 4(9) | 6(5) |

Our experiments indicate useful compositional ranges, by weight, of:
$SiO_2$—44-86%
CaO—4-46%
$P_2O_5$—3-15%.

Use of the above processing technique results in amorphous, glassy gel powders that are chemically stable (e.g., they do not dissolve in aqueous solution). When exposed to simulated body fluids, however, these compositions form a bioactive hydroxyapatite layer on their surfaces. It is also possible to produce glass monoliths instead of powders using known, alternative sol-gel fabrication techniques that may be straightforwardly substituted for the processes described herein; see, e.g., U.S. Pat. Nos. 4,849,378; 4,851,150; or 4,851,373 (the disclosures of which are hereby incorporated by reference).

The powders can also be melted and applied as coatings on sturdy substrates, such as metal, or alumina or other structural ceramics (such as silicon carbide, zirconium oxide or carbon-carbon composites). By varying the amount of $SiO_2$, it is possible to substantially match the thermal expansion coefficients of our compositions with those of compatible substrates. The thermal expansion coefficients associated with the compositions of the present invention vary with the ratio of $SiO_2$ to CaO plus $P_2O_5$ (i.e., $SiO_2/(CaO+P_2O_5)$).

Figure 3:
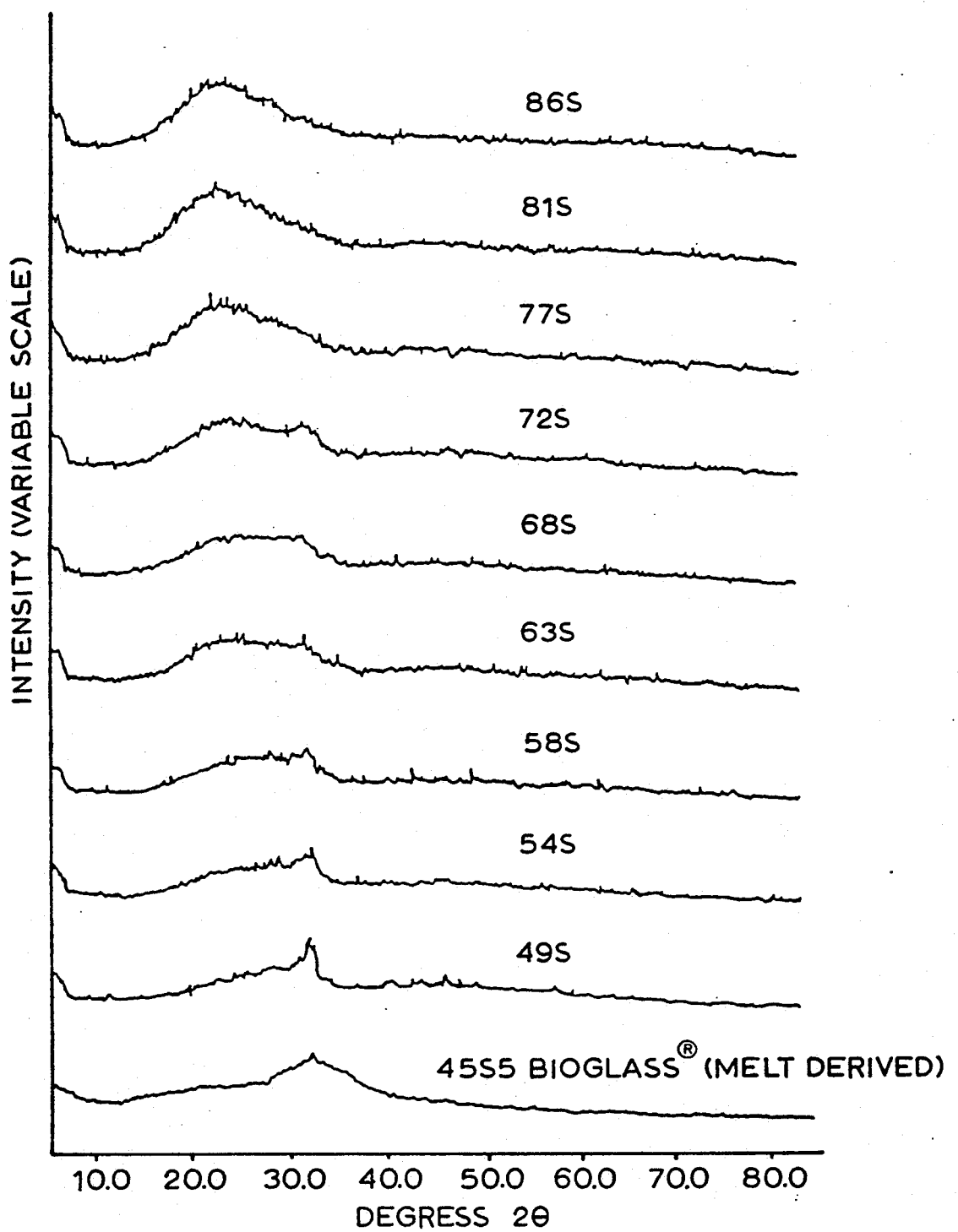
FIG. 3 depicts comparative X-ray diffraction data for the bioactive gel powders listed in Table 1 after heating to 600 degrees Centigrade in accordance with the schedule shown in FIG. 2, and for 45S5 Bioglass® prepared using standard melting and casting.

Evidence of the amorphous, glassy nature of the gels listed in Table 1 is shown in the corresponding X-ray diffraction spectra of FIG. 3. The spectrum of a standard $Na_2O$—CaO—$P_2O_5$—$SiO_2$ bioactive glass (45S5 Bioglass(R)) is shown for comparison. As can be seen from the depicted spectra, the melt-derived glasses show no X-ray diffraction lines, only a very broad peak characteristic of an amorphous solid. The 49S, 54S and 58S samples show a small amount of crystallinity at the main X-ray peak of hydroxyapatite (approximately 32.5 degrees), while all other samples exhibit spectra corresponding to completely amorphous materials.

In order to evaluate the potential bioactivity of the sol-gel powder compositions, each sample was divided evenly by weight into three aliquot portions, and each portion ground using a mortar and pestle into powders of a different particle size: one portion into 25-35 mesh; one portion into 35-45 mesh; and the remaining portion into 45-170 mesh.

The rate of development of the HCA phase on the surface of the glass particles was used as an in-vitro index of bioactivity. The use of this index is based on studies indicating that a minimum rate of hydroxyapatite formation is necessary to achieve bonding with hard tissues. See, e.g., Hench, *Bioactive Ceramics*, in *Bioceramics: Material Characteristics Versus In Vivo Behavior* (P. Ducheyne & J. E. Lemons, Eds., 1988) (hereinafter "Hench 1988"), at 54-71. Both the glass composition and its microstructure exert an influence on the development and growth of the HCA phase. For example, as the $SiO_2$ content of prior-art melt-derived bioactive glasses approaches and exceeds 60 mole percent, the rates of network dissolution, silica repolymerization and hydroxylcarbonate apatite crystallization are retarded; this results in reduction and eventual elimination of bioactivity. The rate of development of the HCA phase on the surface of glass powders can be followed as a function of time utilizing the well-known Fourier Transform Infrared ("FTIR") analysis. See, e.g., Warren, Clark & Hench, *Quality Assurance of Bioglass(R) Powders*, 23 J. Biomed. Mat. Res.-App. Biomat. 201 (1989).

Figure 4A:
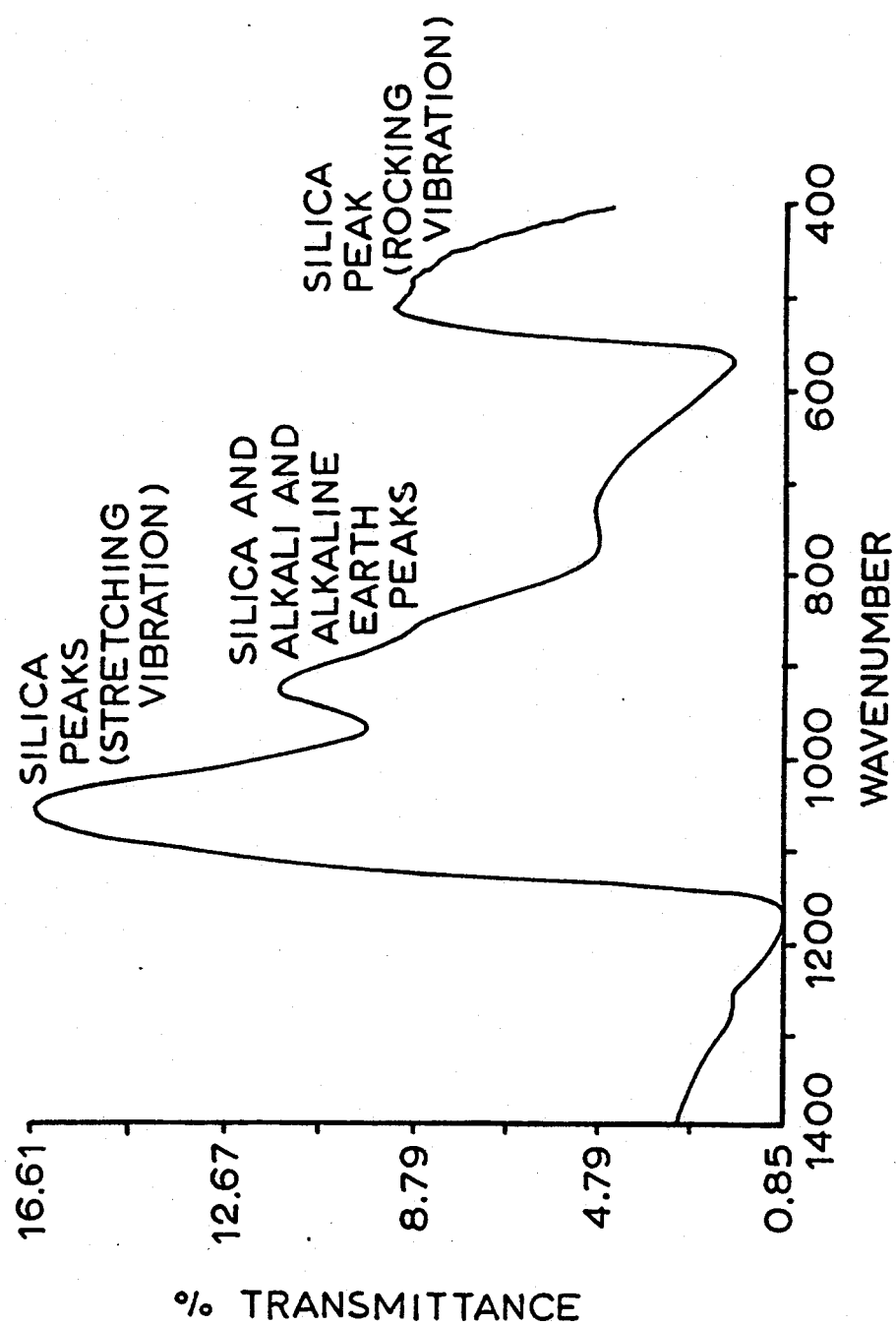
FIG. 4A is an FTIR spectrum for 45S5 Bioglass® powder before reaction in a simulated in-vivo solution.
Figure 4B:
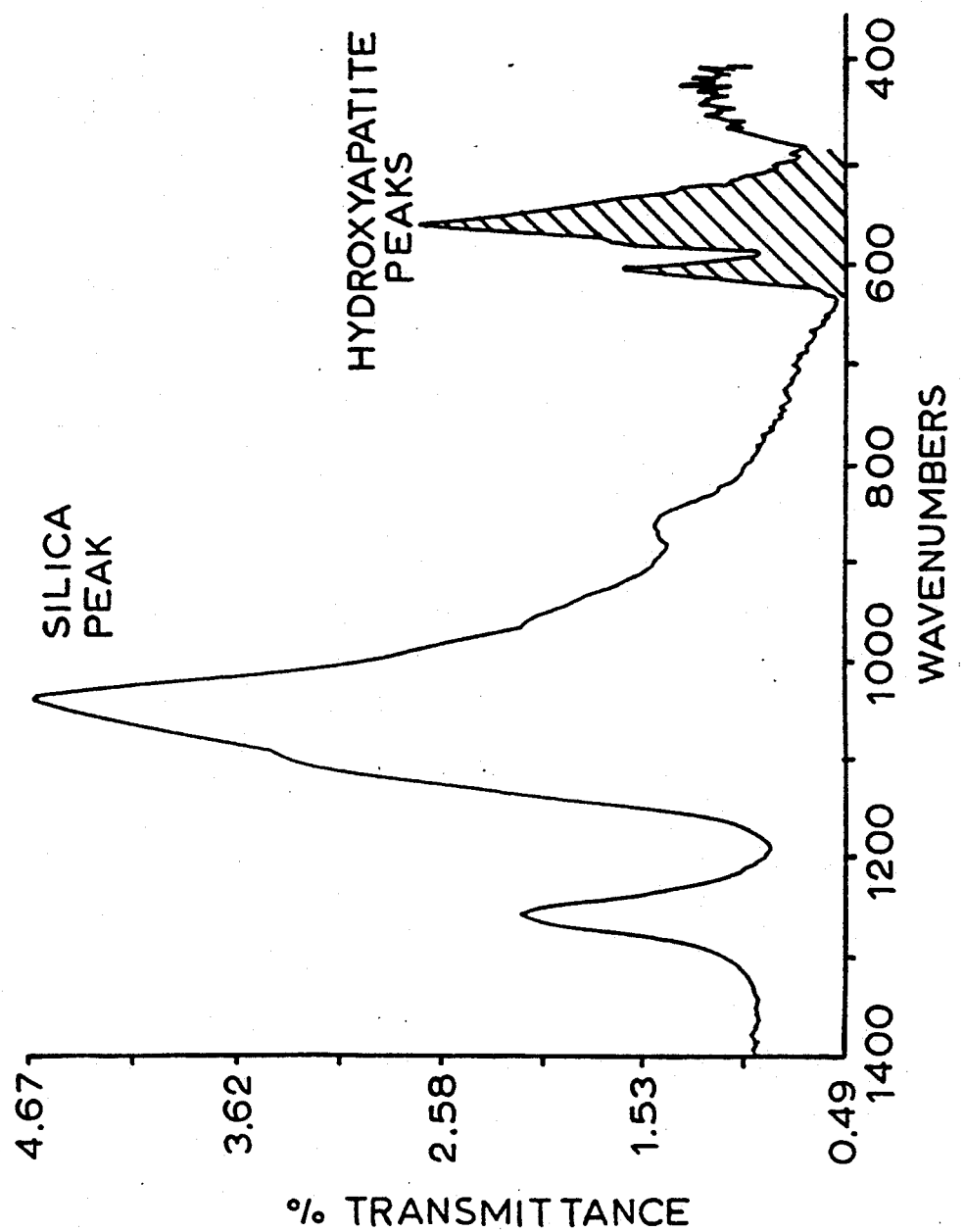
FIG. 4B is an FTIR spectrum for 45S5 Bioglass® powder after 20 hours reaction in simulated in-vivo solution.

We obtained FTIR spectra on standard, melt-derived 45S5 Bioglass(R) powder samples prior to and after a simulated in-vivo solution for 20 hours. The results are presented in FIGS. 4A and 4B, which depict the FTIR spectra of the powder before and after exposure, respectively. As shown in FIG. 4A, vibrational peaks are observed only for silica, silica plus alkali, and alkaline earth before exposure to the solution. However, after exposure and as illustrated in FIG. 4B, the spectrum reveals a pair of strong hydroxyapatite peaks. The silicon-oxygen-silicon rocking vibration peak at 475 cm$^{-1}$ is diminished in the sample after reaction and replaced by the oxygen-phosphorous-oxygen bending vibrations of the hydroxyapatite $PO_4^{-3}$ groups at 598 cm$^{-1}$ and 566 cm$^{-1}$. Because of the very small penetration depth of the infrared beam (less than 1 micron), it can be assumed that the hydroxyapatite peaks arise from a surface layer formed on the powder. Accordingly, these observations indicate that the glass surface has become bioactive.

Figure 5:
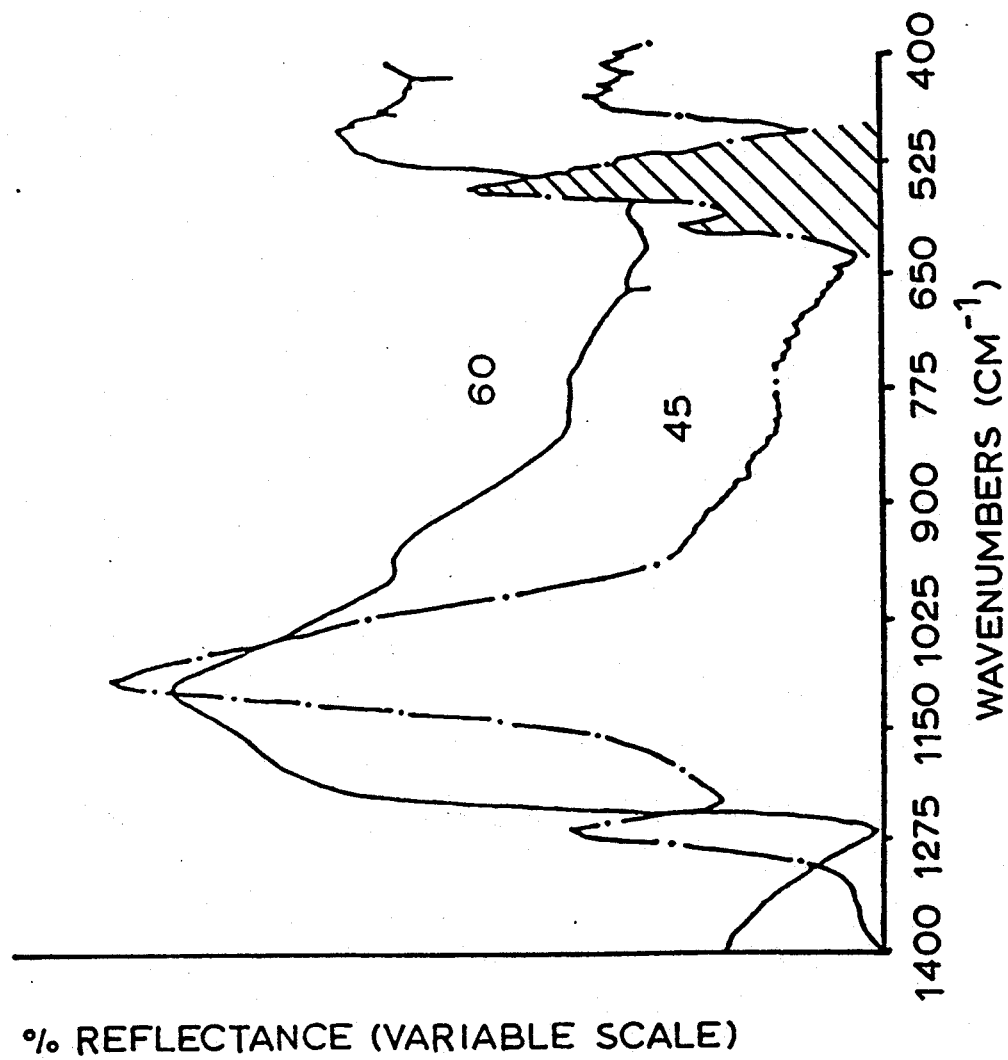
FIG. 5 depicts FTIR spectra for 45S5 Bioglass® and 60S Bioglass®, after 20 hours reaction in simulated in-vivo solution.
Figure 6:
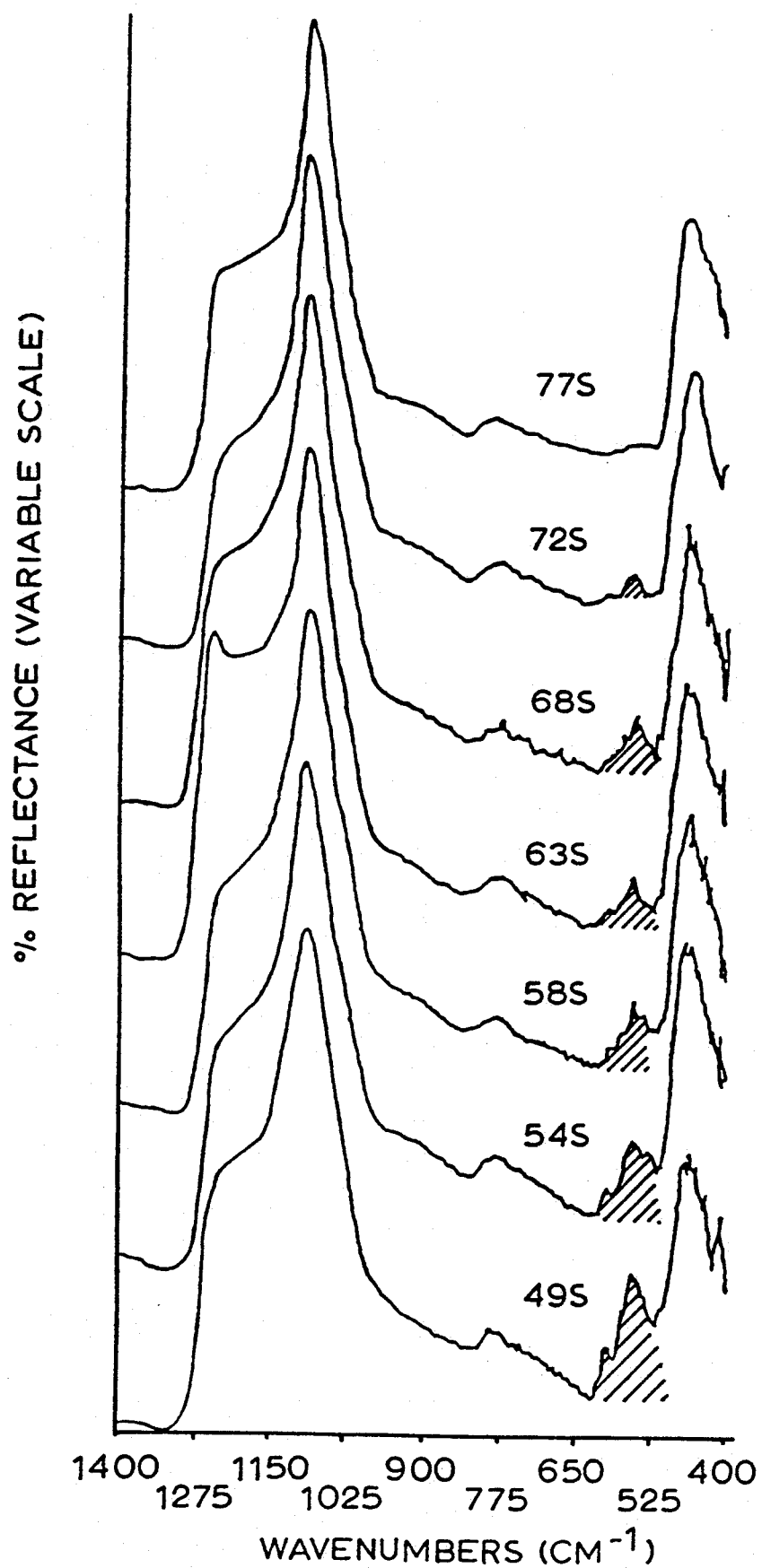
FIGS. 6–9 illustrate changes in the diffuse reflectance spectra of the sol-gel derived bioactive powders after one, two, four and eight hours, respectively, of reaction in simulated in-vivo solution.
Figure 7:
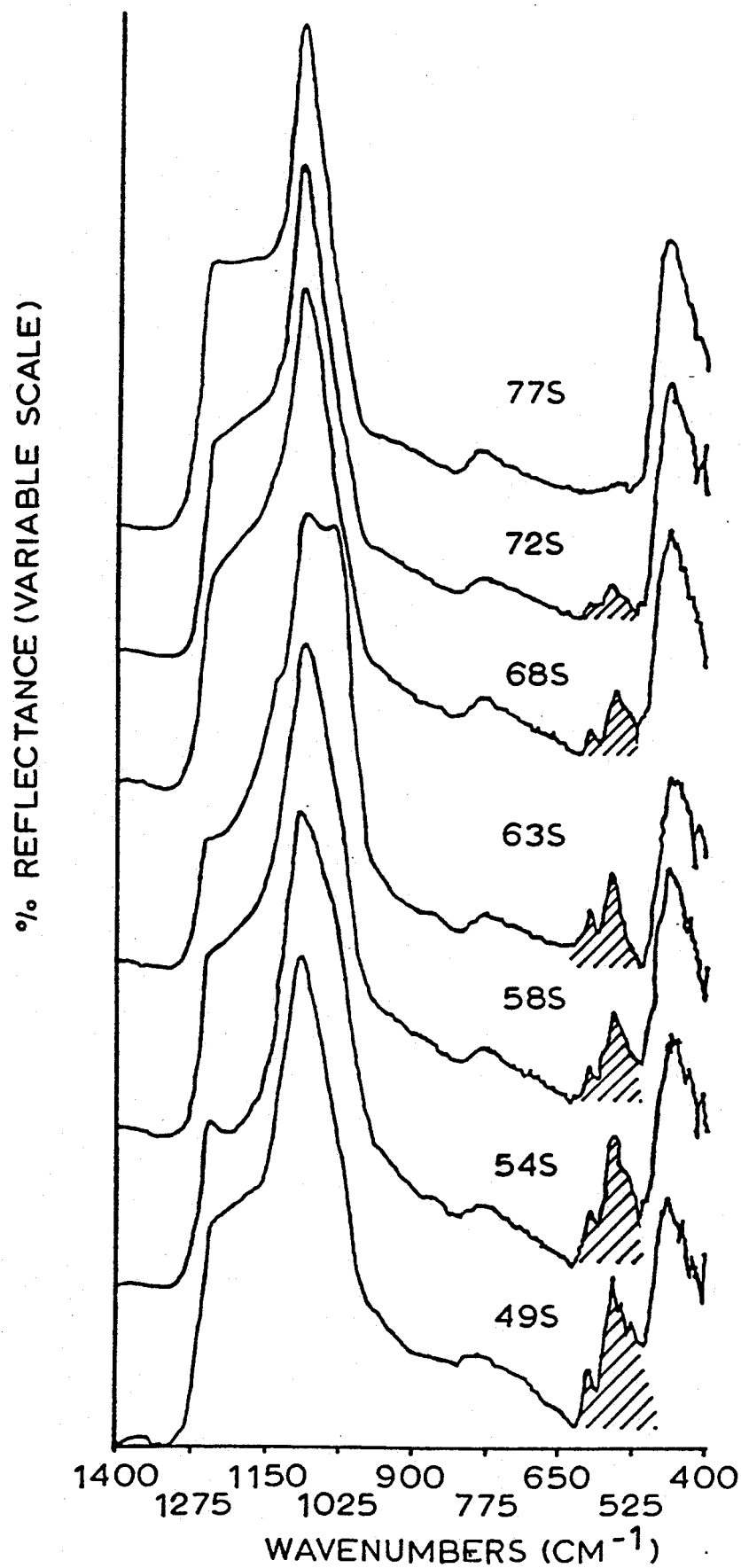
Figure 8:
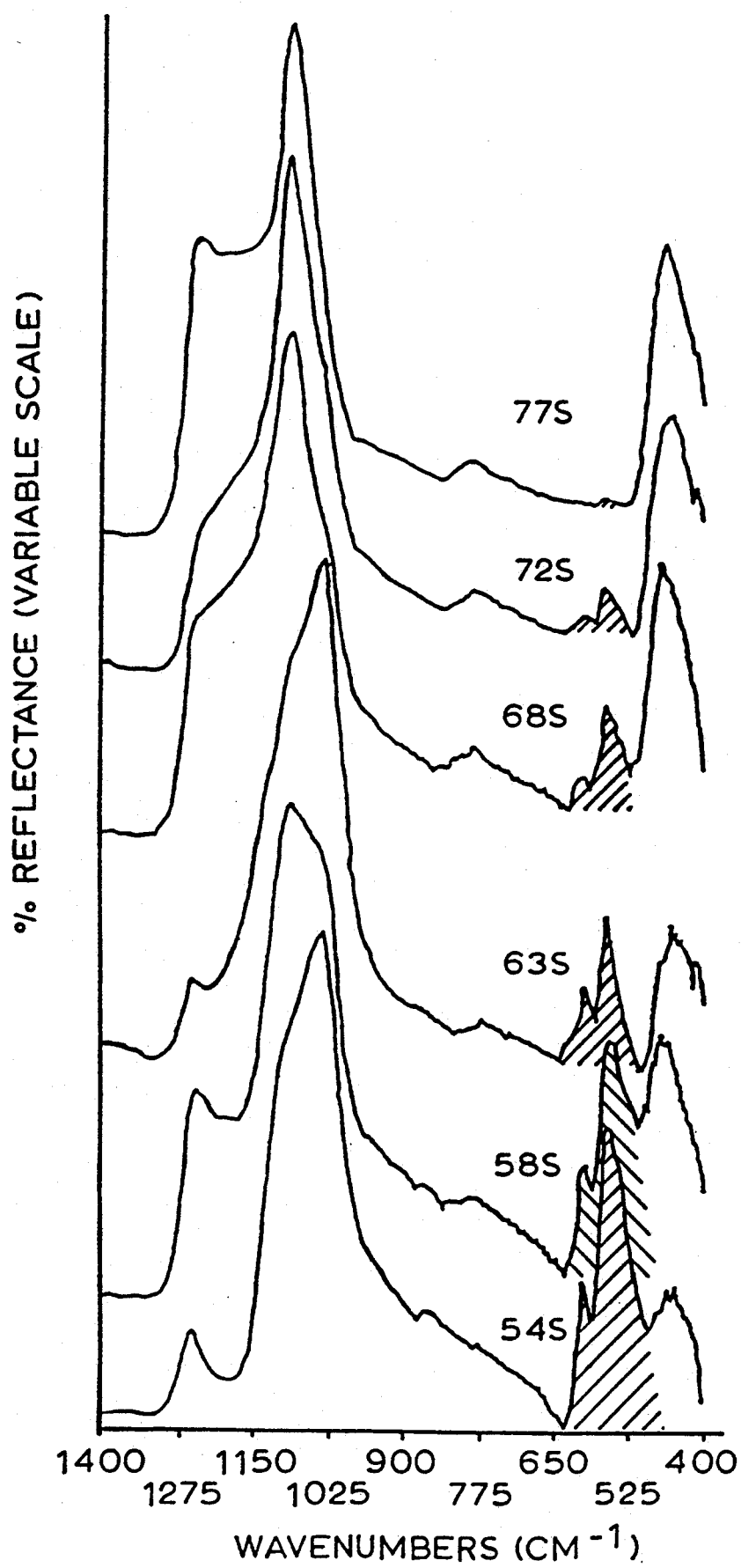

As hereinabove noted, bioactivity tends to diminish with increasing $SiO_2$ content. This is illustrated in FIG. 5, which compares the FTIR spectra of two prior-art melt-derived glasses after reaction in simulated in-vivo solutions at 37 degrees Centigrade, using the same procedure as that described below in connection with sol-gel powders. The 45S5 Bioglass$^{(R)}$ composition (45 weight percent $SiO_2$) forms strong hydroxyapatite peaks after 20 hours. This composition has been observed to be quite bioactive, and bonds both to hard and soft tissues. In contrast, the 60S composition (60 weight percent $SiO_2$) does not develop a hydroxyapatite layer, even after 20 hours in solution. This composition has been observed to lack bioactive properties; it does not bond to bone or to soft tissues. Both of these standard compositions contain $Na_2O$.

The sol-gel derived powders of compositions listed in Table 1 were reacted with tris-buffered solution (pH=7.2+/−0.1, to simulate body fluids) at 37 degrees Centigrade for various times. The powders were immersed directly into the buffered solution in a Nalgene bottle and agitated in an incubator shaker at 37 degrees Centigrade. This test procedure allowed the reacting solution to surround and react with the powders in a reliable and reproducible fashion. We performed FTIR analyses on the reacted powders using a diffuse reflectance stage between 1400 cm$^{-1}$ and 400 cm$^{-1}$ wave numbers.

FIGS. 6 through 9 depict the diffuse reflectance spectra of each bioactive powder at the early stages of reaction (one, two, four and eight hours, respectively). The peaks at 598 cm$^{-1}$ and 566 cm$^{-1}$ represent P—O bending vibrations in $PO_4$ tetrahedra; as discussed previously, these peaks characterize a hydroxyapatite crystalline phase and serve as an indicator of bioactivity.

Figure 9:
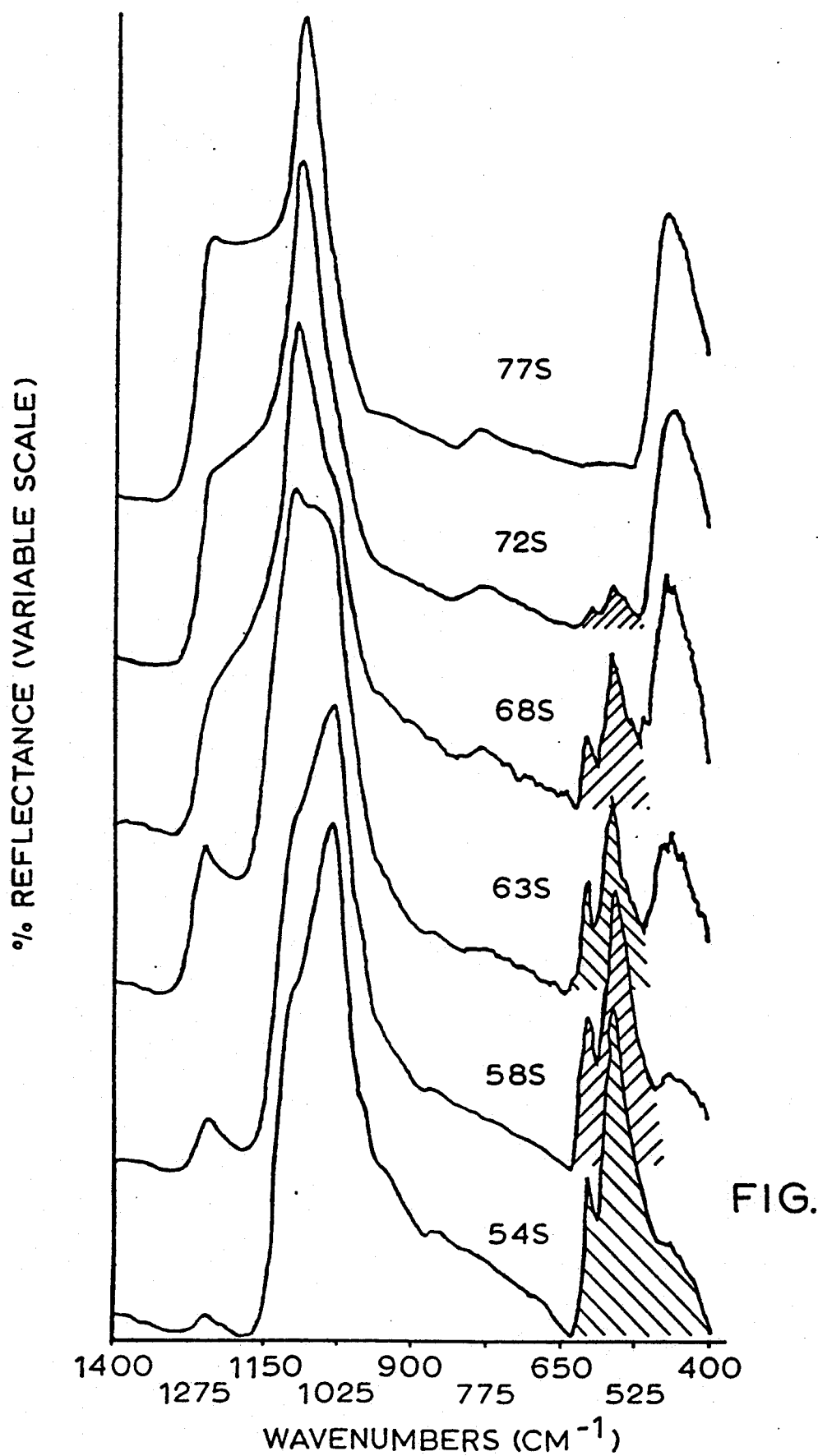

These spectra illustrate the interrelationship between exposure time, $SiO_2$ content and bioactivity. As shown in FIG. 9, development of the P—O peaks is observed within eight hours for sol-gel glasses with a $SiO_2$ content up to 75 mole percent. However, if exposure time is increased to seven days, peaks are observed for glasses containing up to 90 mole percent $SiO_2$; this is illustrated in FIG. 10. Accordingly, variation of preliminary exposure periods facilitates great flexibility in achieving biocompatibility with a wide range of $SiO_2$ proportions; conversely, the constituents of our compositions can be varied in proportion to achieve a desired rate of hydroxyapatite formation (and hence bioactivity).

Without being bound to any particular theory or mechanism, we believe that the enhanced compositional range of bioactivity obtainable with the present invention derives from the presence of small pores (approximately 1.2 to 10 nm) and large surface area of the sol-gel derived powders, as shown in the following table:

TABLE 2

| Sample | Surface Area (m$^2$g) | Total Pore Volume (cc/g) | Average Pore Size (angstroms) |
|---|---|---|---|
| 49S | 203 | 0.57 | 57 |
| 54S | 213 | 0.53 | 50 |
| 58S | 289 | 0.49 | 34 |
| 63S | 320 | 0.49 | 27 |
| 68S | 326 | 0.41 | 25 |
| 72S | 380 | 0.38 | 20 |
| 77S | 431 | 0.32 | 15 |
| 81S | 547 | 0.37 | 14 |
| 86S | 627 | 0.45 | 14 |

These ultrastructural features give rise to a large area density of nucleation sites for hydroxyapatite crystallites. With this favorable deposition environment, buildup of a hydroxyapatite layer can take place at higher rates and with lower proportional concentrations of CaO and $P_2O_5$ than would be necessary for ordinary bioactive glass compositions. Consequently, bioactive glasses can be prepared with relatively large levels of $SiO_2$ that exhibit relatively small local pH variations in vivo.

Previous investigations of bioactive glass compositions that bond to bone demonstrate that bonding occurs within 10 to 30 days if the surface area developed in simulated test solutions falls within the range of 200–500 m$^2$/g; see, e.g., U.S. Pat. No. 4,171,544. The compositions of the present invention all exhibit surface areas greater than 200 m$^2$/g (although we believe that the surface area can be reduced below this level while still retaining sufficient rates of hydroxyapatite formation). The growth of the hydroxyapatite film with exposure to simulated in-vivo solutions further augments these surface areas.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A bioactive composition prepared using a sol-gel process, and consisting essentially of more than 60 but no more than 86 weight percent $SiO_2$, at least 4 but less than 33 weight percent CaO and at least 3 but no more than 15 weight percent $P_2O_5$.

2. The composition of claim 1 wherein the bioactive glass forms a hydroxyapatite layer upon exposure to body fluids.

3. The composition of claim 1, wherein the bioactive glass is produced as a powder using a sol-gel process.

4. The composition of claim 1, wherein the bioactive glass is produced as a monolith using a sol-gel process.

5. The composition of claim 1, wherein the bioactive glass is produced as a coating using a sol-gel process.

6. A bioactive glass powder consisting essentially of $SiO_2$, CaO and $P_2O_5$, prepared using a sol-gel process, and having pores with a diameter range of from about 1.2 to about 10 nm and a surface area of at least 200 m$^2$/g, wherein the weight percentage of $SiO_2$ is more than 60 but no more than 86, the weight percentage of CaO is at least 4 but less than 33, and the weight percentage of $P_2O_5$ is at least 3 but no more than 15.

* * * * *

UNITED STATES PATENT AND TRADEMARK OFFICE
CERTIFICATE OF CORRECTION

PATENT NO. : 5,074,916
DATED : December 24, 1991
INVENTOR(S) : Larry L. Hench, et. al.

It is certified that error appears in the above-indentified patent and that said Letters Patent is hereby corrected as shown below:

On the Title page, item [73], Assignee: should read as follow:
University of Florida
223 Grinter Hall
Gainesville, Florida  32611

Signed and Sealed this

Twenty-second Day of November, 1994

Attest:

BRUCE LEHMAN

*Attesting Officer*  *Commissioner of Patents and Trademarks*